(12) United States Patent
Davison et al.

(10) Patent No.: US 6,361,488 B1
(45) Date of Patent: Mar. 26, 2002

(54) SUPPORT APPARATUS FOR ENDOSCOPIC SURGERY

(75) Inventors: Thomas Davison; Adam Sher, both of North Attleboro; Gene P. DiPoto, Upton; John D. Unger, Wrentham, all of MA (US)

(73) Assignee: Endius Incorporated, Plainville, MA (US)

( * ) Notice: Subject to any disclaimer, the term of this patent is extended or adjusted under 35 U.S.C. 154(b) by 0 days.

(21) Appl. No.: 09/491,808

(22) Filed: Jan. 28, 2000

(51) Int. Cl.[7] ................................................ A61B 1/00
(52) U.S. Cl. ........................ 600/102; 600/114; 606/130
(58) Field of Search ............................... 600/102, 114; 606/130; 604/264

(56) References Cited

U.S. PATENT DOCUMENTS

| | | | |
|---|---|---|---|
| 5,520,607 A | * 5/1996 | Frassica et al. | ............. 600/102 |
| 5,571,072 A | * 11/1996 | Kronner | ................... 600/102 |
| 5,792,044 A | * 8/1998 | Foley et al. | ................. 600/114 |
| 5,954,635 A | 9/1999 | Foley et al. | |
| 6,007,487 A | 12/1999 | Foley et al. | |
| 6,152,871 A | 11/2000 | Foley et al. | |
| 6,162,170 A | 12/2000 | Foley et al. | |
| 6,176,823 B1 | 1/2001 | Foley et al. | |
| 6,206,822 B1 | 3/2001 | Foley et al. | |
| 6,217,509 B1 | 4/2001 | Foley et al. | |

* cited by examiner

Primary Examiner—Linda C. M. Dvorak
Assistant Examiner—Jocelyn D. Ram
(74) Attorney, Agent, or Firm—Tarolli, Sundheim, Covell, Tummino & Szabo L.L.P.

(57) ABSTRACT

An apparatus (10) for use in percutaneous surgery includes a cannula (11), a first support (20), and a second support (40). The cannula (11) has a channel (12) extending into the cannula (11). The channel (12) has a central axis (14). The first support (20) is associated to the cannula (11) and has a circular perimeter (21) which has a center (22) on the central axis (14). The second support (40) supports a viewing element (200) which extends into the channel (12). The second support (40) is rotatable about the center (22) of the circular perimeter (21) of the first support (20) relative to the first support (20).

42 Claims, 9 Drawing Sheets

SUPPORT APPARATUS FOR ENDOSCOPIC SURGERY

TECHNICAL FIELD

The present invention relates to an apparatus for use in percutaneous surgery.

BACKGROUND OF THE INVENTION

Percutaneous surgery is a procedure in which surgical instruments and typically an endoscope are inserted through a cannula into the body of a patient. A viewing element, typically a small video camera, is part of the endoscope and is connected to a television monitor so that the surgeon may view the surgical sight.

The cannula is a hollow tube. The cannula is inserted through an incision into the body of a patient. The instruments, usually one at a time, and the endoscope are inserted through the cannula. The cannula also allows the instruments and endoscope to be removed from the body and/or adjusted in the body during the surgery.

A conventional apparatus for supporting the cannula and the endoscope allows a surgeon to manipulate the surgical instruments without also moving the endoscope. Also, a known support apparatus allows adjustment of the endoscope relative to the cannula for viewing different areas in the body.

SUMMARY OF THE INVENTION

In accordance with one feature of the present invention, an apparatus for use in percutaneous surgery includes a cannula, a first support, and a second support. The cannula has a channel extending into the cannula. The channel has a central axis. The first support is associated with the cannula and has a circular perimeter, which has a center on the central axis of the channel extending into the cannula. The second support supports a viewing element, which extends into the channel. The second support is rotatable about the center of the circular perimeter of the first support relative to the first support and the cannula.

In accordance with another feature of the present invention, an apparatus for use in percutaneous surgery includes a cannula having a channel extending into the cannula. The channel has a central axis. A first support is associated with the cannula. A mechanism connects the first support and the cannula for relative movement along the central axis. The mechanism comprises a gripper for gripping the cannula, a connection member connected to the gripper, and an adjustable member for moving the connection member and the gripper mechanism relative to the first support along the central axis.

In accordance with still another feature of the present invention, an apparatus for use in percutaneous surgery includes a cannula having a channel extending into the cannula. The channel has a central axis. A first support is associated with the cannula. A second support supports a viewing element, which extends into the channel. A structure connecting the first and second supports includes a movable member for repositioning the first and second supports relative to each other along said central axis.

In accordance with yet another feature of the present invention, an apparatus for use in percutaneous surgery includes a cannula having a channel extending into the cannula. A mechanism for supporting the cannula includes a support arm for attachment to a vacuum controlled mechanical arm to which vacuum is applied to prevent relative movement of parts of the mechanical arm. A valve is actuatable to vent the vacuum applied to the mechanical arm through the support arm, and a manually movable member is connected to the support arm and actuates the valve to vent the vacuum applied to the mechanical arm through the support arm.

In accordance with still another feature of the present invention, an apparatus for use in percutaneous surgery includes a cannula, a support, and a mechanism. The cannula has a channel extending into the cannula. The cannula has a central axis. The support supports a viewing element which extends into the channel. The mechanism adjusts the position of the viewing element in a direction transverse to the central axis.

BRIEF DESCRIPTION OF THE DRAWINGS

The foregoing and other features of the present invention will become more apparent to one skilled in the art upon consideration of the following description of the invention and the accompanying drawings in which.

DESCRIPTION OF A PREFERRED EMBODIMENT

As representative of the present invention, the Figures illustrate an apparatus 10 for use in percutaneous surgery including a cannula 11, a first support 20, a second support 40, a first adjustment mechanism 60, a second adjustment mechanism 80, and a third adjustment mechanism 100.

The cannula 11 is a cylindrical metal or plastic tube with a channel 12 extending completely through the cannula 11. The channel 12 has a central axis 14. The cannula is inserted through an incision into a body of a patient during surgery. One end portion of the cannula is expandable in the body of the patient as shown in an advertisement entitled "Endius® Spine Endoscopy System with FlexPosure™." The cannula is also disclosed in U.S. patent application Ser. No. 09/137,335, Filed Aug. 20, 1998.

Figure 4:
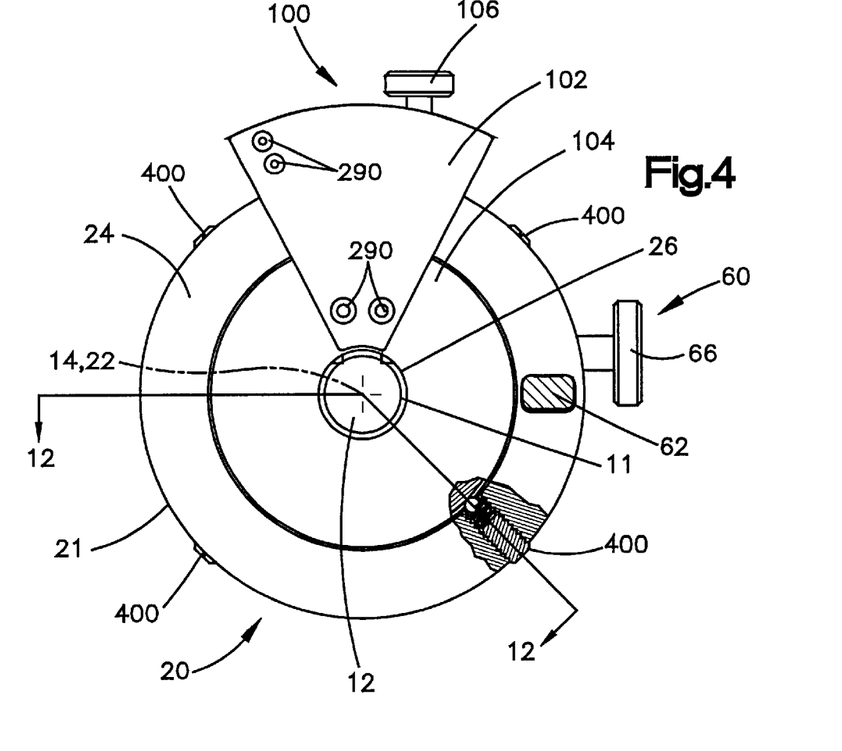
FIG. 4 is a schematic view taken along line 4—4 in FIG. 1 showing part of the apparatus of FIG. 1.
Figure 12:
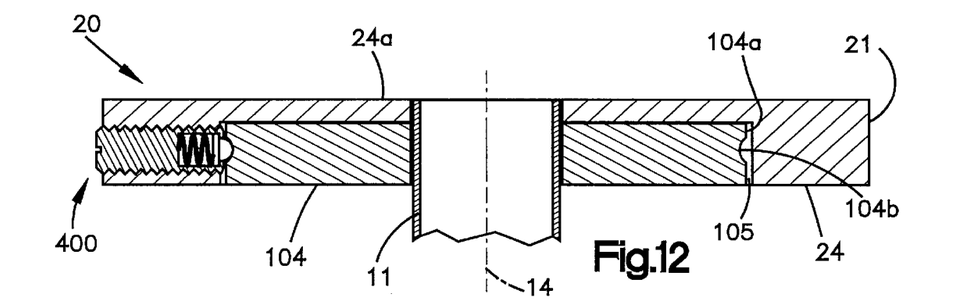
FIG. 12 is a sectional view taken approximately along line 12—12 of FIG. 4.

As viewed in FIGS. 4 and 12, the first support 20 is associated with the cannula 11 and has a circular perimeter 21. The perimeter 21 has a center 22 located on the central axis 14. The first support 20 comprises a circular platform, or disk 24, which has a circular opening 26 in the central area of the disk 24 for receiving an end portion 16 of the cannula 11. The circular opening 26 has a center located on the central axis 14. The end portion 16 of the cannula 11 can be easily inserted into and removed from the opening 26. The disk 24 has a projection portion 20a, which is located adjacent the perimeter 21 of the disk 24. The disk 24 has an upper circular surface area 24a, which surrounds the opening 26.

Figure 10:
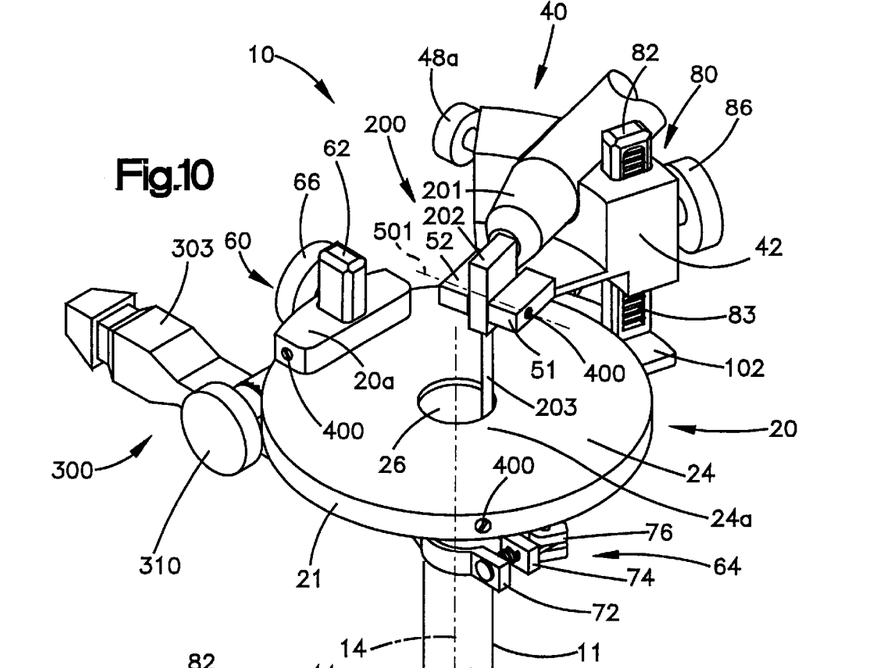
FIG. 10 is a perspective view of the apparatus of FIG. 1 looking at the apparatus from an angle different than FIG. 9.

As viewed in FIG. 10, the second support 40 connects to a viewing device 200 consisting of a camera head 201 and an endoscope 202 with a rod and lens assembly 203, herein referred to as a viewing element, extending down into the channel 12 of the cannula 11. The second support 40 includes a body 42 having an opening 44 through which the viewing device 200 extends and a clamp 46 for clamping the viewing device 200 to the body 42 in the opening 44. The clamp 46 includes a threaded set screw 48 for securing the viewing device 200 to the body 42. The set screw 48 has a manually rotatable knob 48a and a stem threaded into the body 42. When rotated, the screw 48 moves axially relative to the body 42 to clamp or release the viewing device 200 depending on the direction of rotation of the screw 48.

Figure 3:
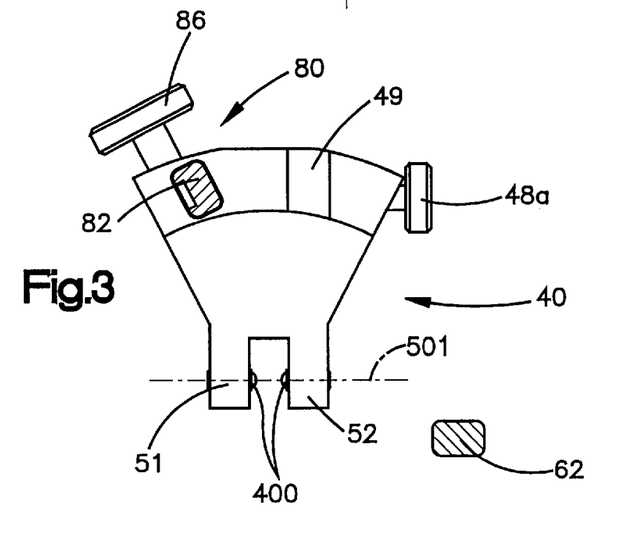
FIG. 3 is a schematic view taken along line 3—3 in FIG. 1 showing part of the apparatus of FIG. 1.

The body 42 of the second support 40 further includes two extension arms 51, 52 (FIG. 3) for supporting the endoscope 202. Each extension arm 51, 52 includes a threaded bore for receiving a resilient detent member, or ball plunger 400.

Figure 13:
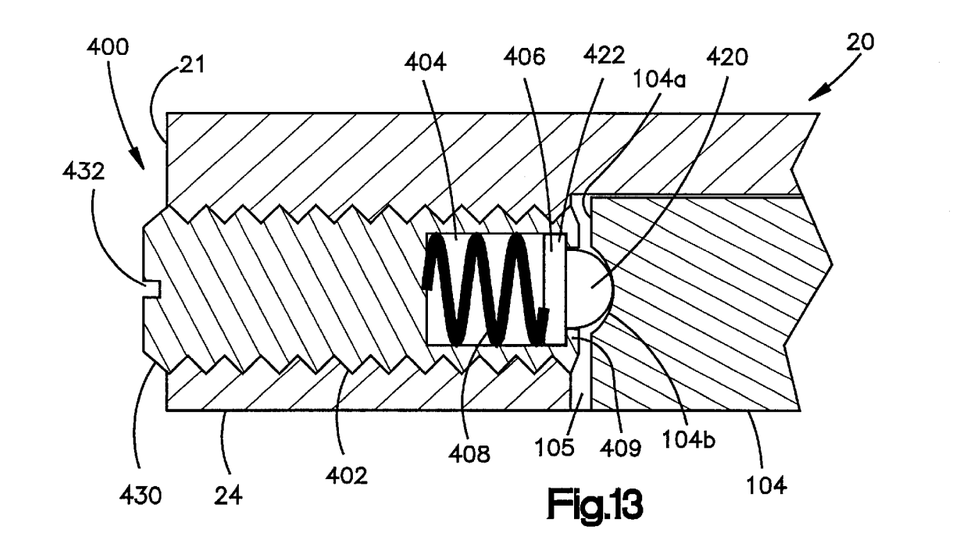
FIG. 13 is an enlarged view of a part of FIG. 12.

As viewed in FIGS. 12 and 13, a ball plunger 400 is illustrated at another location in the apparatus 10. Each ball plunger 400, including those in the extension arms 51, 52, has an externally threaded tubular body 402 with a cylindrical cavity 404 located therein. The cavity 404 houses a projection 406 and a coiled spring 408. The projections 406 of the two ball plungers 400 of the extension arms 51, 52 are spherical detent members 420 in the form of balls (not shown). The spring 408 urges each projection 406 against a lip portion 409 of the body 402. The lip portion 409 is located at one end of the cavity 404. As shown in FIG. 13, the other ball plungers 400 of the apparatus 10 have project ions 406 with hemispherical extensions 420 and shoulder portions 422.

As viewed in FIG. 10, the endoscope 202 has corresponding hemispherical recesses (not shown) for receiving the spherical detent members (balls) of the ball plungers 400 which are located in extension arms 51, 52. The springs 408 will compress in each ball plunger 400 in each extension arm 51, 52 and the spherical detent members will move inward of each cavity 404 and then spring back into the hemispherical recesses in the endoscope 202, as the endoscope 202 is inserted between the extension arms 51, 52. The entire viewing device 200 will thus be secured between the extension arms 51, 52, but may be removed by overcoming the force of the spherical detent members of each ball plunger 400 in the extension arms 51, 52.

The ball plunger 400 further includes a head portion 430 with a slot 432 for engaging a tool, such as a screwdriver. The ball plunger 400 may be threadedly adjusted within the threaded bore of either extension arm 51, 52 to alter the distance that the spherical detent member 420 projects away from the extension arms 51, 52 (toward each other). This distance, along with the stiffness of each spring 408, will determine the holding force by which the endoscope 202 is secured between the extension arms 51, 52.

The first adjustment mechanism 60 provides for relative axial adjustment of the cannula 11 and first support 20 along the central axis 14. The first adjustment mechanism 60 includes a first toothed rack member 62, a cannula gripper mechanism 64 fixedly connected to the first rack member 62, a first manually adjustable, rotatable knob 66 rotatably carried by the projection portion 20a of the first support 20, and a first gear member 65 (FIG. 7) rotatable by the first knob 66 and in meshing engagement with the teeth 63 of the first rack member 62. The first support 20 and, in particular, the projection portion 20a, rotatably carries the first gear member 65 (FIG. 7).

Figure 1:
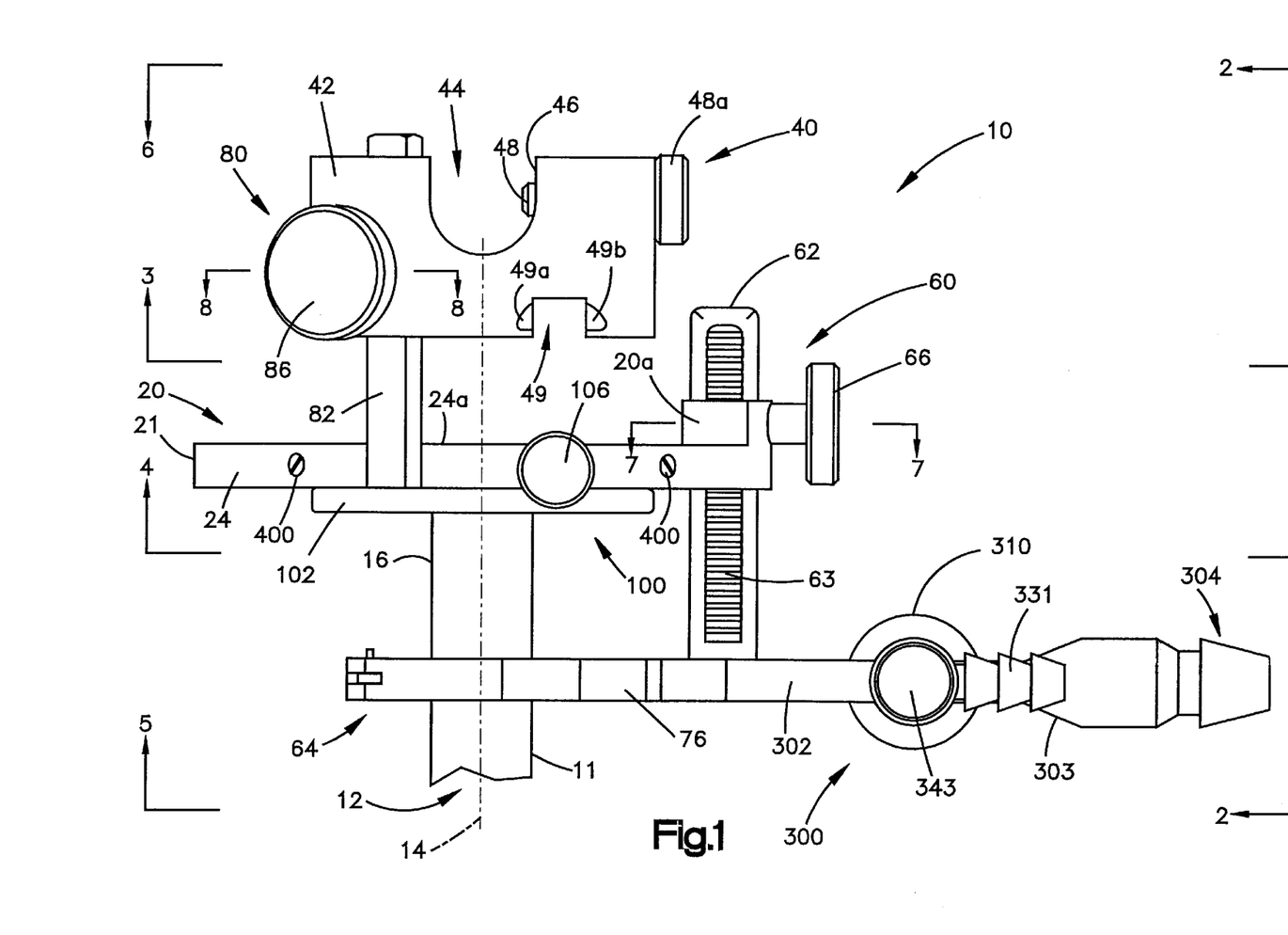
FIG. 1 is a schematic view of an apparatus embodying the present invention.
Figure 2:
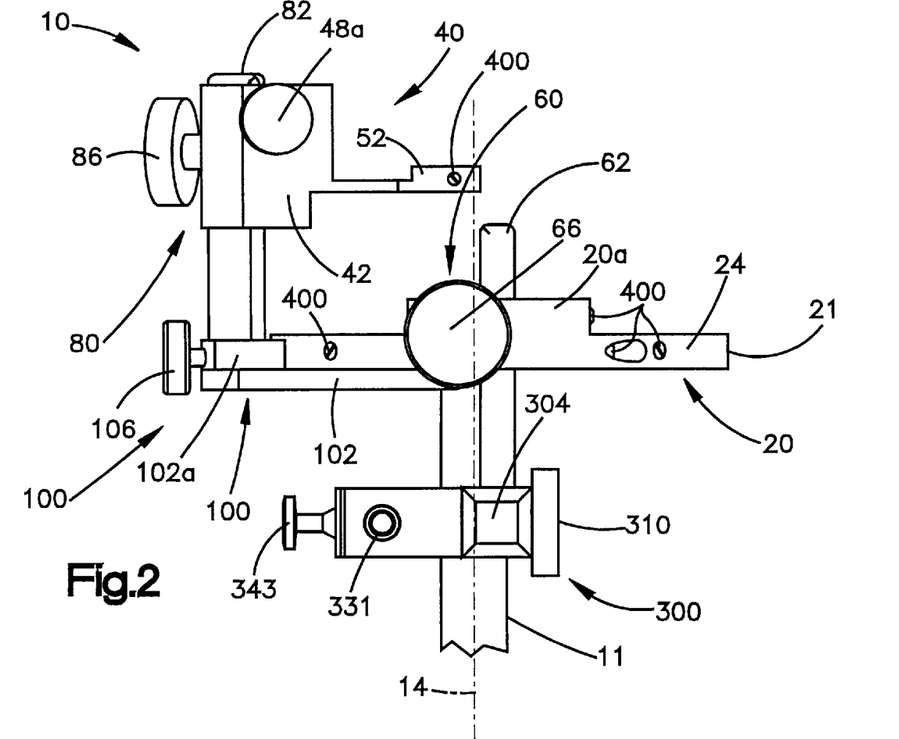
FIG. 2 is a schematic view taken along line 2—2 in FIG. 1.
Figure 7:
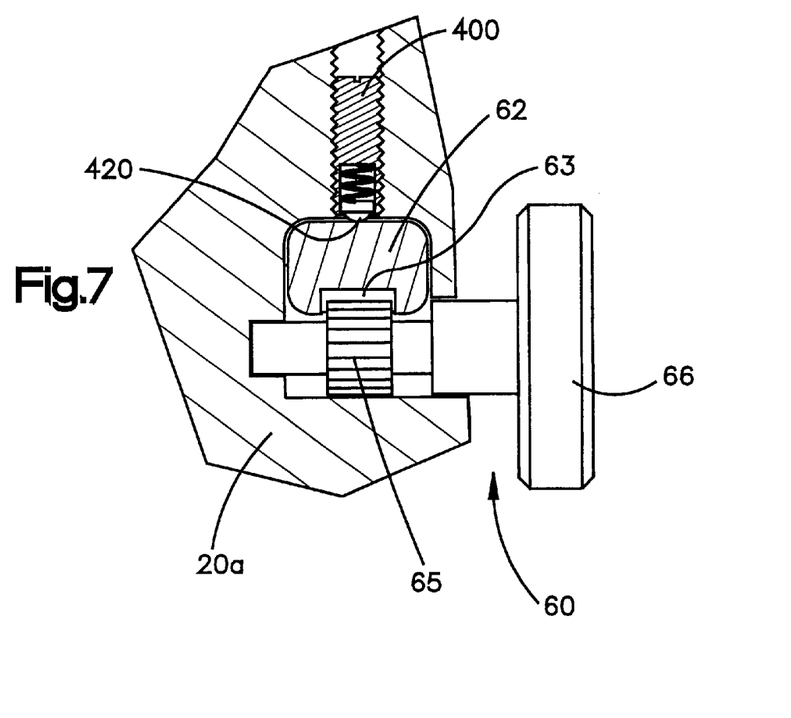
FIG. 7 is a schematic view taken along line 7—7 in FIG. 1 showing part of the apparatus of FIG. 1.

The first rack member 62 is secured to slide axially within the first support 20 and the projection portion 20a by two ball plungers 400 (FIG. 7). One ball plunger 400 is tangentially threaded into a tapered, threaded bore (FIG. 2) in the perimeter 21 of the first support 20 and the other is tangentially threaded into a threaded bore in the projection portion 20a. The hemispherical extensions 420 thus frictionally engage a smooth portion (without teeth 63) of the first rack member 62 and bias the first rack member 62 against the first support 20 and the projection portion 20a. This biasing also maintains the engagement of the first rack member 62 and the first gear member 65 (FIG. 7).

Figure 5:
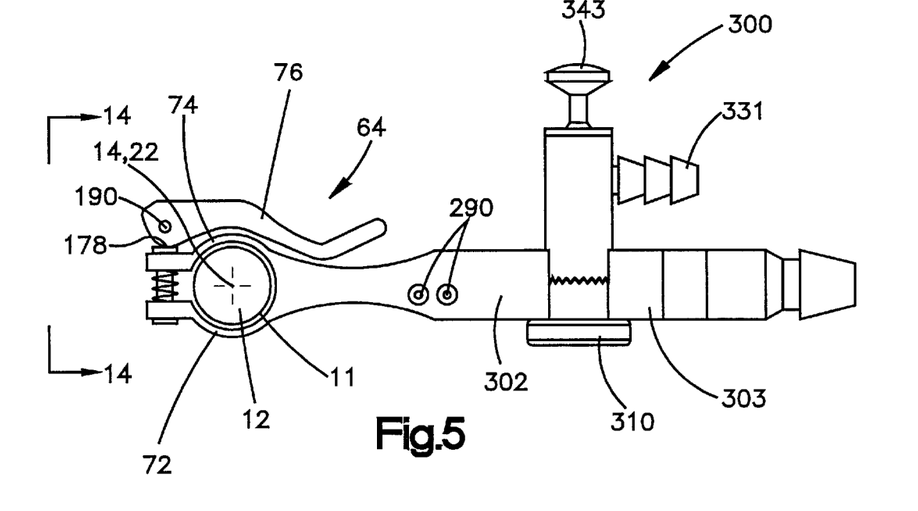
FIG. 5 is a schematic view taken along line 5—5 in FIG. 1 with parts removed.
Figure 6:
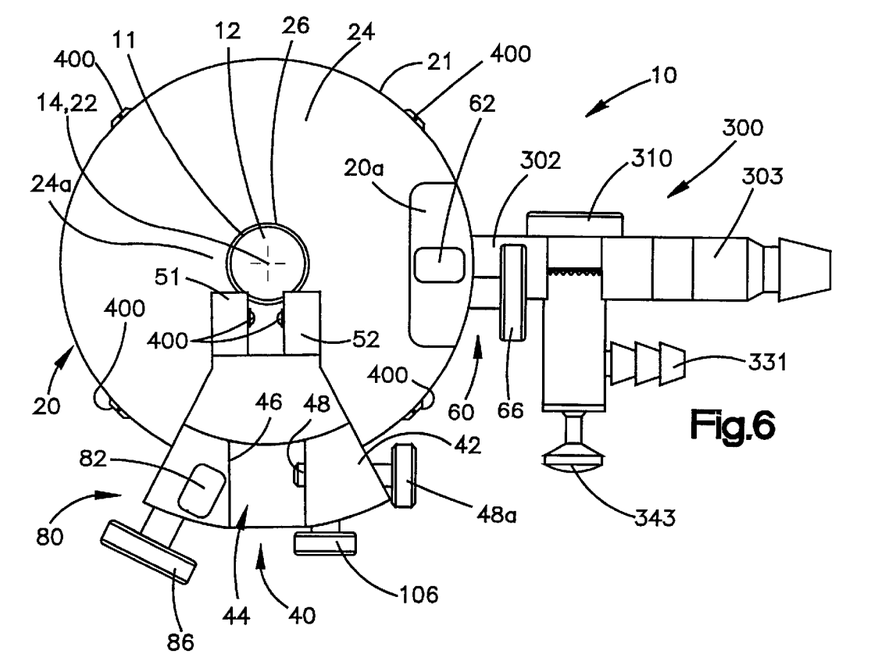
FIG. 6 is a schematic view taken along line 6—6 in FIG. 1.
Figure 14:
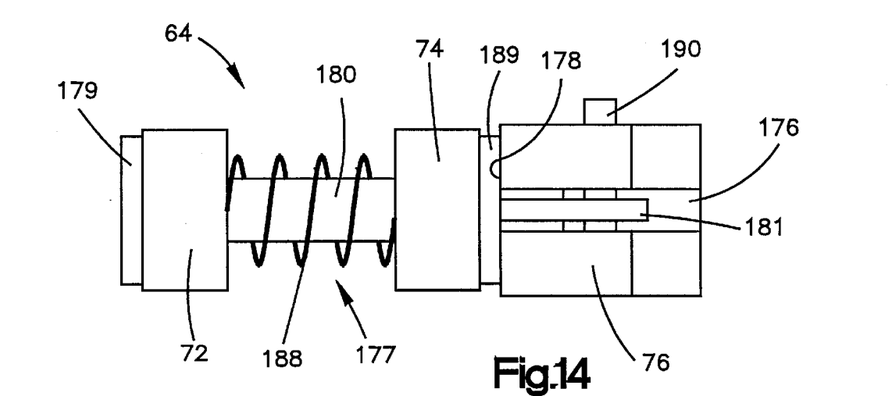
FIG. 14 is a schematic view taken along line 14—14 in FIG. 5 with parts removed.

As viewed in FIGS. 5 and 14, the cannula gripper mechanism 64 includes two gripper arms 72, 74 for clamping against the outer surface of the cannula 11, and a gripper actuating lever 76 for moving the arms 72, 74 into engagement with the outer surface of the cannula 11 and for releasing the arms 72, 74 from engagement with the cannula 11.

As viewed in FIG. 14, the cannula gripper mechanism 64 further includes a support pin 177, a coiled spring 188, a washer 189 with a bore (not shown), and a lock pin 190. The support pin 177 has a head 179, a shaft 180, and an oblong, or flat end 181 which can mate with the bore in the washer 189. This structure could be different.

During assembly, the coiled spring 188 is interposed between the arms 72, 74. The flat end 181 of the support pin 177 is inserted through a circular bore in the first clamp arm 72, through the coil of the spring 188, through a circular bore in the second arm 74, and through the bore in the washer 189. The flat end 181 of the support pin 177 is then inserted into a slot 176 in the lever 76. The lock pin 190 is inserted through a bore in the lever 76 and through a bore in the flat end 181 of the support pin 177 thereby securing the mechanism 64 together and allowing the lever 76 to rotate about the lock pin 190. A camming surface 178 on the lever 76 adjacent the washer 189 forces the arms 72, 74 together to grip the cannula 11 as the lever 76 is rotated clockwise (as viewed in FIG. 5). Counterclockwise rotation of the lever 76 allows the spring 188 to force the arms 72, 74 apart and releases the cannula 11 from the gripper mechanism 64.

When the gripper mechanism 64 is either gripping the cannula 11 or released from the cannula 11 and the knob 66 is rotated, the disk 24 and parts attached to the disk 24 will move along the axis 14 of the cannula 11 relative to the cannula 11. After the apparatus 10 is initially lined up with the cannula 11. The viewing device 200 may be positioned on the apparatus 10 and adjusted along the cannula axis 14 by rotation of knob 66.

The second adjustment mechanism 80 provides axial adjustment of the first and second supports 20, 40 relative to each other along the central axis 14. The second adjustment mechanism 80 includes a second toothed rack member 82 connected to the first support 20, a second manually adjustable, rotatable knob 86 rotatably carried by the body 42 of the second support 40, and a second toothed gear member 85 (FIG. 8) rotatable by the second knob 86 and in meshing engagement with the teeth 83 of the second rack member 82. The second support 40, and in particular, the body 42, rotatably carries the second gear member 85 (FIG. 8).

The body 42 of the second support 40 may have a notch 49 which can fit around part 102a of the third adjustment mechanism 100 and allow the lower surface of the body 42 to completely abut the disk 24 as the body 42 is brought into an axial position adjacent the disk 24.

Figure 8:
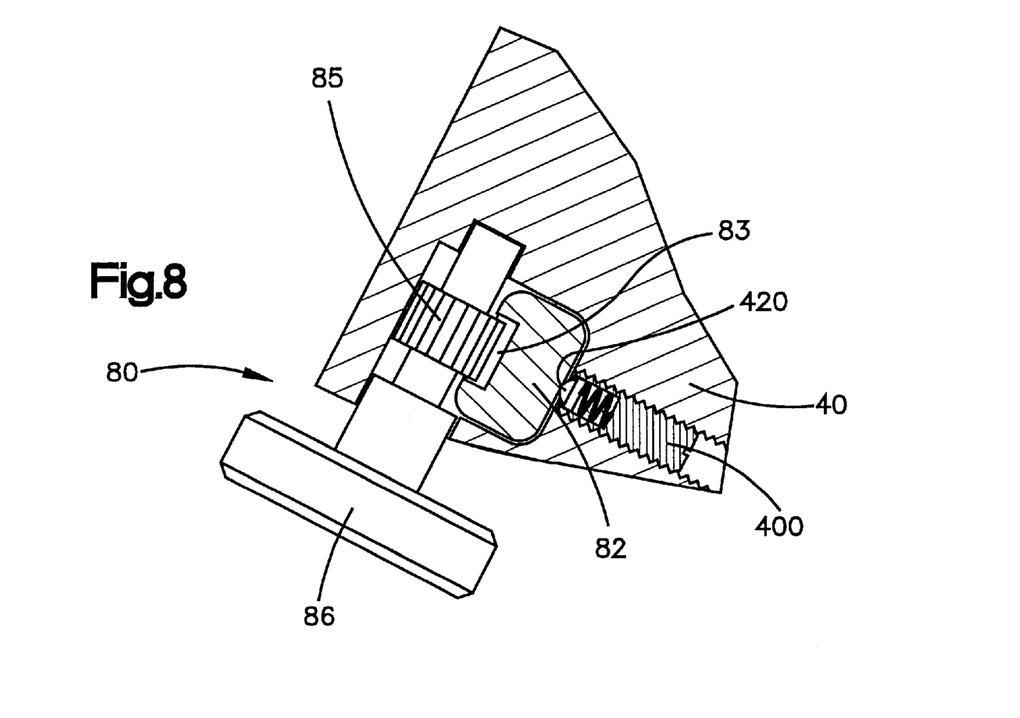
FIG. 8 is a schematic view taken along line 8—8 in FIG. 1 showing part of the apparatus of FIG. 1.
Figure 9:
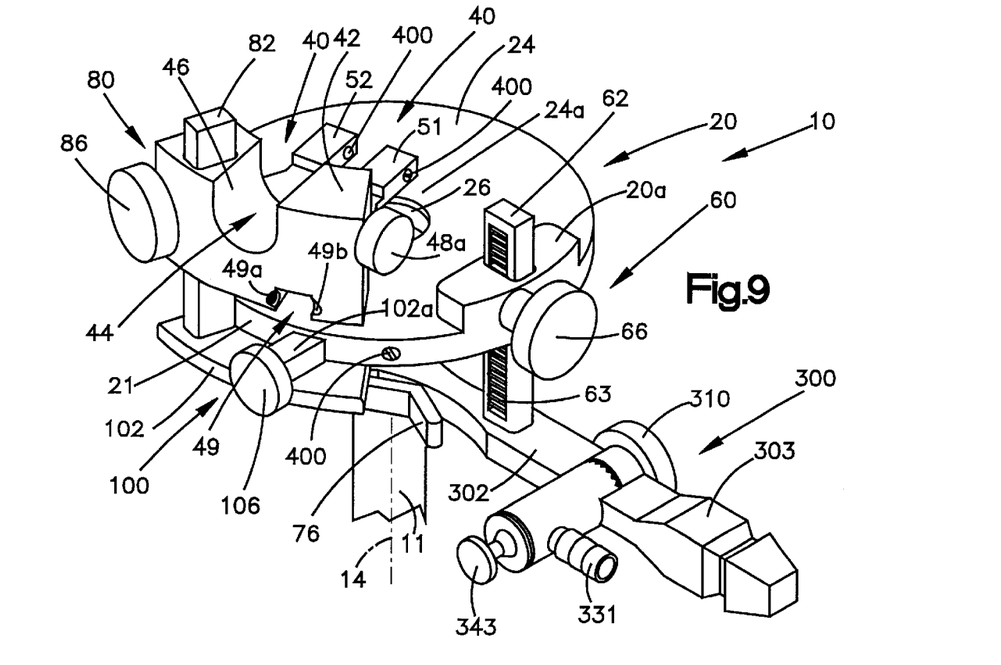
FIG. 9 is a perspective view of the apparatus of FIG. 1.

The second rack member 82 is secured to slide axially within the second support 40 by a ball plunger 400 (FIG. 8). The ball plunger 400 is tangentially threaded into a threaded bore in the side of the notch 49 of the second support 40. The hemispherical extension 420 thus frictionally engages a smooth portion (without teeth 83) of the second rack member 82 and biases the second rack member 82 against the second support 40. The biasing also maintains the engagement of the second rack member 82 and the second gear member 85. Both sides of the notch 49 have tapered portions 49a, 49b for facilitating insertion of the ball plunger 400 into the threaded bore of the notch 49 of the second support 40. Rotation of the knob 86 causes the body 42 and the viewing device 200 attached thereto to move relative to the cannula 11 and disk 24 along the central axis 14.

The third adjustment mechanism 100 provides arcuate, circumferential adjustment of the second support 40 about the central axis 14 relative to the first support 20. The third adjustment mechanism 100 includes a wedge-shaped support member 102 (FIG. 4) fixedly connecting the second rack member 82 to a ring member 104 which is rotatably supported by the first support 20 and rotatable about the central axis 14 relative to the first support 20 (FIG. 12).

The third adjustment mechanism further includes a third manually adjustable, rotatable knob 106 which is part of a set screw. The set screw is rotatably threaded into a projection portion 102a of the support member 102 and is engageable with the circular perimeter 21 of the disk 24 of the first support 20 to lock the support member 102 in an arcuate position relative to the first support 20 and the central axis 14.

As viewed in FIGS. 12 and 13, the ring member 104 is supported within a cylindrical, open ended recess 105 of the first support 20. The recess 105 is concentric about the central axis 14. The perimeter 104a of the ring member 104 has a groove 104b for engaging a plurality of ball plungers 400 (preferably four equally spaced apart) in the first support 20. Each of these ball plungers 400 is similar in construction. Each ball plunger 400 is threaded radially into the perimeter 21 of the first support 20 to provide a hemispherical extension 420 extending into the recess 105 of the first support 20.

The ring member 104 thus is biasingly supported within the recess 105 of the first support 20 and can rotatably slide within the recess 105 about the central axis 14. The ball plungers 400 operatively support the ring member 104 in the recess 105 of the first support 20. The ring member 104, along with the second support 40 and the second and third adjustment mechanisms 80, 100, can be easily removed from the recess 105 for cleaning, maintenance, etc. of the parts by overcoming the force applied by the ball plungers 400 to the ring member 104. When the knob 106 is rotated to disengage the perimeter 21 of disk 24, the body 42 and parts connected thereto can be manually rotated about the central axis 14. This causes the viewing device 200 to rotate about the axis 14 of the cannula 11 and enables the surgeon to view different parts of the surgical sight as desired.

Figure 11:
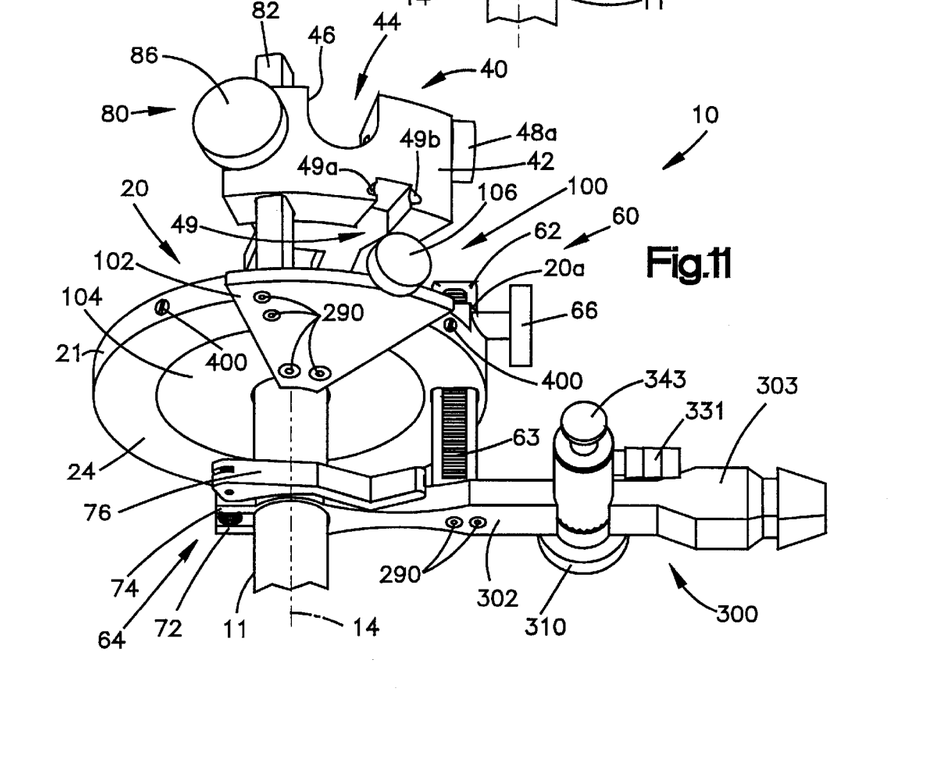
FIG. 11 is a perspective view of the apparatus of FIG. 1 looking at the apparatus from an angle different than FIGS. 9 and 10.

As viewed in FIG. 11, the fixed connections of the first rack member 62 to a support arm 300, the second rack member 82 to the wedge-shaped support member 102, and the support member 102 to the ring member 104 may be made by one or more suitable metal fasteners 290, such as rivets or bolts. The entire apparatus 10 can be constructed from metal or any other suitable material having sufficient mechanical strength and durability. Certain parts may be made from materials permitting X-rays and other techniques for viewing the surgical sight (i.e., radiopaque parts). Other parts may also be made from non-magnetic materials to reduce electromagnetic interference (i.e., electromagnetic insulating parts).

Figure 15:
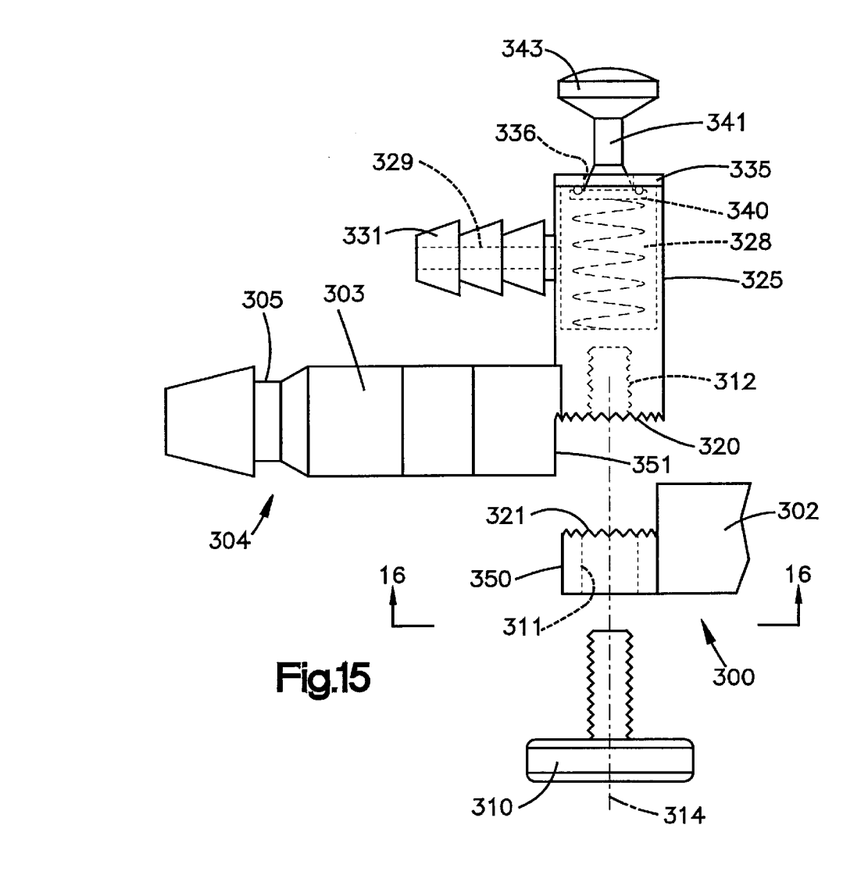
FIG. 15 is a view further illustrating parts shown in FIG. 5.
Figure 16:
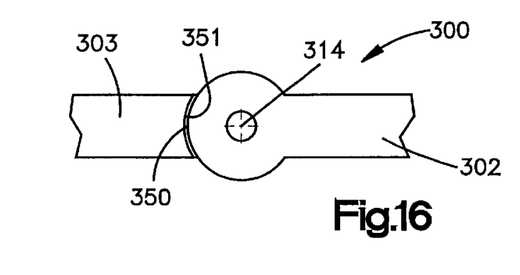
FIG. 16 is a view taken approximately along line 16—16 of FIG. 15.
Figure 17:
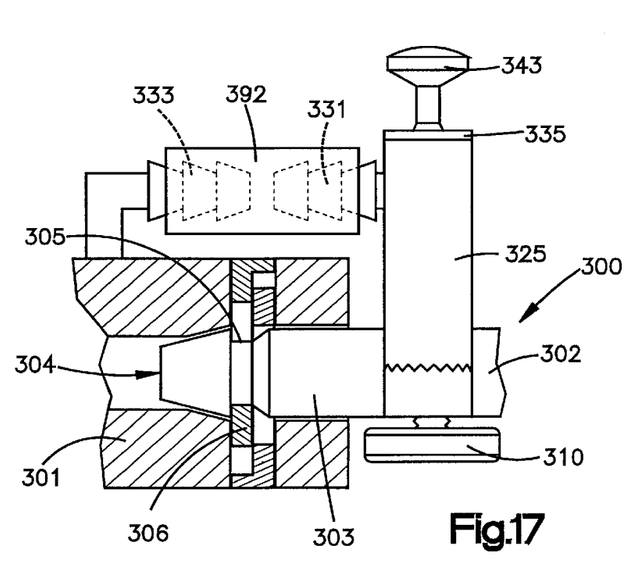
FIG. 17 is a schematic view showing the apparatus of the present invention with an associated known mechanical arm.

As viewed in FIGS. 15–17, the grippers arms 72, 74 are a part of the support arm 300 for attaching the apparatus 10 to a mechanical robotic arm 301. The support arm 300 includes an arm portion 302 which is formed integrally with the arms 72, 74. The arms 72, 74 are integrally constructed with the arm portion 302.

The support arm 300 also includes an arm portion 303. The arm portion 303 has an attaching structure 304, including a groove 305, which snaps into a socket in the mechanical arm 301. Detents of any suitable type and designated 306 in the mechanical arm 301, hold the arm portion 303 in position in the socket in the mechanical arm 301. The detents 306 may be controlled by external actuation levers (not shown) on the mechanical arm 301 for manually releasing the arm portion 303 from the mechanical arm 301.

The arm portions 302 and 303 are pivotally connected to each other by a fastener 310. The fastener 310 extends through an opening 311 in the arm portion 302 and threads into a threaded opening 312 in the arm portion 303. When the fastener 310 is released, the arm portions 302, 303 may pivot relative each other about a pivot axis 314. The pivot axis 314 is centered on the axis of the fastener 310 and the axis of the threaded opening 312. When the fastener 310 is tightly screwed into the threaded opening 312, the arm portions 302, 303 are secured together against pivoting movement. When the fastener is released, the arm portions 303, 302 may pivot relative to each other about the axis 314.

The end of the arm portion 302, which is adjacent to the arm portion 303, has a convex surface 350, which is curved about the axis 314. The arm portion 303 has a concave surface 351, which is also curved about the axis 314. The surfaces 350, 351 move concentrically relative to each other when the arm portions 303 and 302 pivot relatively about the axis 314.

The arm portion 303 has a set of teeth 320 which encircle the axis 314 and which project axially toward a set of teeth 321 on the arm portion 302. The teeth 321 project axially toward the teeth 320. The teeth 320 and the teeth 321 mesh with each other and provide a locking action so that the arm portions 302, 303 are positively locked against relative movement about axis 314 when the fastener 310 is tightly screwed into the opening 312. The teeth 320, 321 comprise a lock which blocks relative rotation of the arm portions 302, 303 about the axis 314. When the fastener 310 is loosened, the arm portions 302, 303 may be rotated relative to each other about the axis 314, and thus, the arm portions 302, 303 may pivot relative to each other to adjust the position of the apparatus 10.

A cylindrical projection 325 is welded to the arm portion 303. Thus, the projection 325 and arm portion 303 are fixedly connected together. The projection 325 is centered on the axis 314 and contains a chamber 328.

As viewed in FIG. 17, the chamber 328 communicates with a fluid passage 329 in a male fluid connector 331. The male connector 331 attaches to a male connector 333 on the mechanical arm 301 by means of a flexible hose 392 so that the fluid passage 329 communicates with a fluid passage in the mechanical arm 301.

As viewed in FIG. 15, the chamber 328 is closed at its upper end by a cap 335. The cap 335 has an opening 336 centered on the axis 314. The opening 336 communicates with the chamber 328. A manually movable internal valve member 340 normally closes the opening and blocks the chamber 328 from communicating with the ambient air surrounding the support arm 300. The valve member 340 is connected to a stem 341, which is also centered on the axis 314. The stem 341 has a knob or button 343 on its end which may be manually depressed to move the stem 341 and valve member 340 downward into the chamber 328. When the stem 341 and valve member 340 are so moved, the chamber 328 is in communication with the ambient air surrounding the device due to the unblocking of the opening 336.

The mechanical arm 301 is a known device and is of the type generally disclosed in U.S. Pat. No. 4,863,133. The mechanical arm 301 is sold by Leonard Medical, Inc. 1464 Holcomb Road, Huntington Valley, Pa., 19006. The mechanical arm 301 includes relatively movable parts, which permit movement and adjustment of the apparatus 10 in a variety in planes, directions, and orientations. The mechanical arm 301 permits easy movement when a vacuum is not applied to the arm 301. When a vacuum is applied to the arm 301, relative movement of the parts of the arm 301 is resisted, and therefore adjustment of the apparatus 10 is difficult.

When the button 343 is depressed, the chamber 328 loses its vacuum and the pressure in the chamber 328 increases toward ambient pressure. The passage 329 communicates this pressure increase to the mechanical arm 301, and thus the parts of the mechanical arm 301 are free to move and allow for adjustment of the position of the apparatus 10 by the surgeon.

Accordingly, when the surgeon uses the apparatus 10, the support arm 300 is snapped into the socket of the mechanical arm 301 where it is held by the detent 306. The surgeon may then depress the button 343 and relatively move parts of the mechanical arm 301 as well as the apparatus 10 into the position where the surgeon desires the apparatus 10 to be. This position may be where the opening 26 in the disk 24 is aligned with the end portion 16 of the cannula 11 with the opposite end portion of the cannula 11 being located in an incision in the body of a patient. The viewing device 200 may be mounted on the apparatus 10, and the surgeon may make adjustments prior to and during the surgical procedure as desired, as described above.

Figure 18:
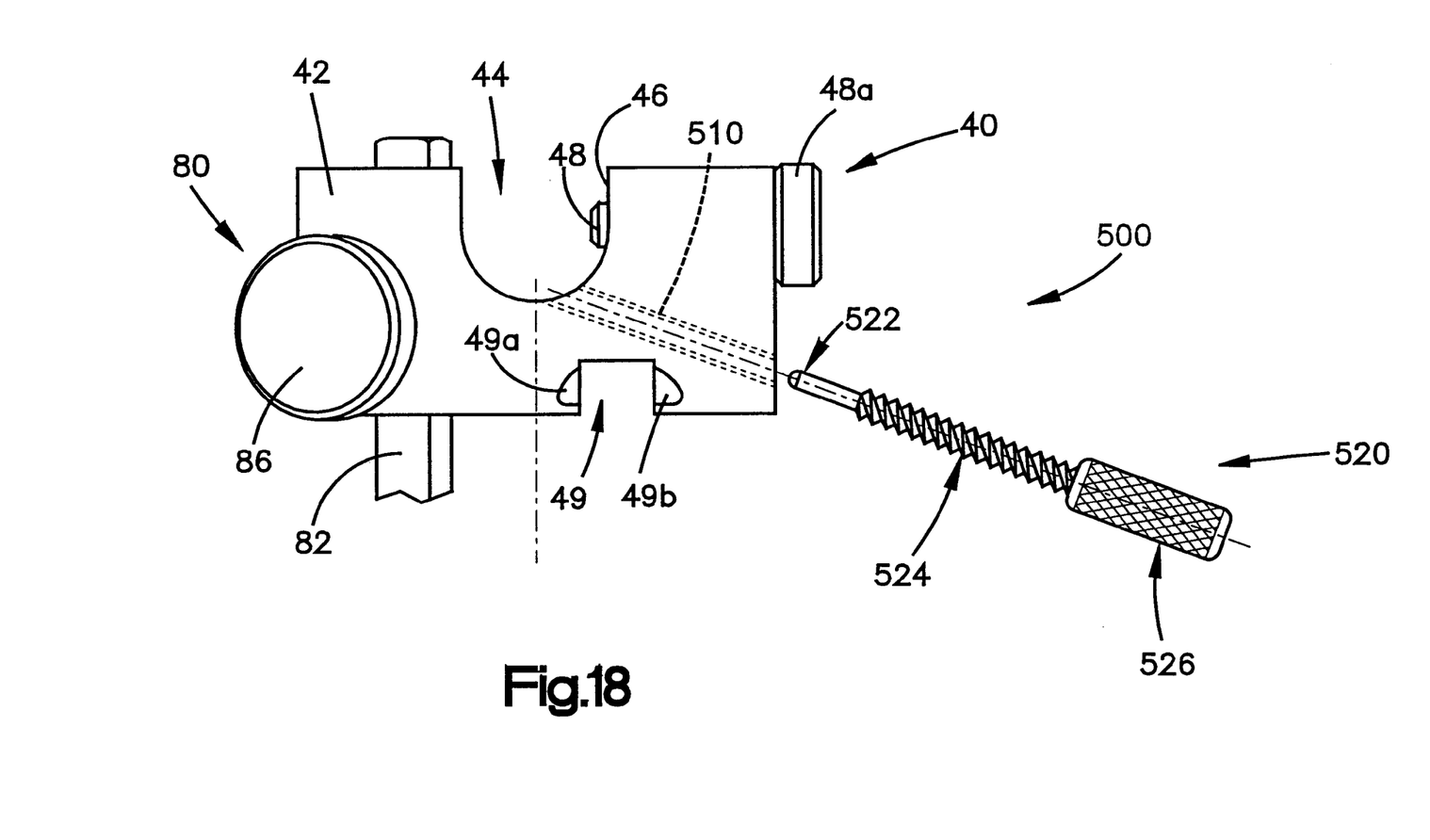
FIG. 18 is a schematic view of another feature of part of the apparatus of FIG. 1.

As viewed in FIG. 18, the apparatus 10 may include a second support 40 with a fourth adjustment mechanism 500 for rotating the viewing device 200 about an axis 501 (FIG. 10) defined by the ball plungers 400 of the extension arms 51, 52 when set screw 48 is not clamping the viewing device 200 to the body 42. The axis 501 is offset from the axis 14 of the cannula 11 and perpendicular to the axis 14 of the cannula 11. Rotation of the viewing device 200 about axis 501 causes the endoscope 202 and the rod and lens assembly 203 to move perpendicular to the central axis 14 of the cannula 11. This rotation will result in radial adjustment of the position of the rod and lens assembly 203 in a radial direction transverse to the central axis 14.

The spring-loaded connections of the spherical detent members 420 of the ball plungers 400 and the hemispherical recesses of the endoscope 202 allow rotation about the axis 501 when the set screw 48 is released from clamping engagement of the viewing device 200.

The mechanism 500 includes a threaded bore 510 in the second support 40 and an adjustable member 520 for moving (vertically as viewed in the FIGS.) a part of the viewing device 200 about the axis 501. The adjustable member 520 has a rounded first end portion 522, a threaded middle portion 524, and a knurled second end portion 526, or knob. The bore 510 extends at an angle as shown in FIG. 18 from a lower portion of the second support 40 up to the opening 44 in the clamp 46 of the second support 40.

The adjustable member 520 is rotated and threaded into the bore 510 and may be rotated until the first end portion 522 protrudes into the opening 44 of the second support 40. Accordingly, when the surgeon wishes to adjust the rod and lens assembly 203 (within the surgical sight) about the axis 501 and radially relative to the axis 14 of the cannula 11, the surgeon may loosen the connection of the set screw 48 with the viewing device 200 and rotate the adjustable member 520 by manually rotating knob 526 so that the first end portion 522 vertically extends farther or less into the opening 44. This adjustment will adjust the part of the viewing device 200 engaged by the clamp 46 along the central axis 14, rotate the viewing device 200 about the axis 501, and cause the lens 203 at the surgical sight to move transverse to the axis 14 of the cannula 11. This will expand the area of the surgical sight which the surgeon may view. When the adjustment is complete, the surgeon may tighten the set screw 48 and re-secure the viewing device 200 to the second support 40 of the apparatus 10.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for use in percutaneous surgery, said apparatus comprising:

a cannula having a channel extending through said cannula, said channel having a central axis;

a first support associated with said cannula, said first support at least partially having a circular perimeter, said perimeter having a center on said central axis, said first support having an opening for said cannula; and a second support for supporting a viewing element which extends into said channel, said second support being rotatable about said center relative to said first support.

2. The apparatus as defined in claim 1 wherein said first support comprises a circular disk, said disk having an at least partially circular surface area extending transverse to said central axis.

3. The apparatus as defined in claim 1 wherein said second support comprises a body having an opening through which said viewing element extends and a clamp for clamping said viewing element in said opening.

4. The apparatus as defined in claim 3 further including a first rack member, a cannula gripper mechanism connected to said first rack member, a first manually rotatable knob carried by said first support, and a first gear member rotatable by said first knob and in meshing engagement with said first rack member, rotation of said knob causing adjustment of said first support relative to said cannula in a direction parallel to said central axis.

5. The apparatus as defined in claim 4 further including a mechanism for moving said body of said second support relative to said first support in a direction parallel to said central axis.

6. The apparatus as defined in claim 5 wherein said mechanism includes a second rack member connected to said first support, a second manually rotatable knob carried by said body of said second support, a second gear member rotatable by said second knob and in meshing engagement with said second rack member, said second gear member carried by said body of said second support and in meshing engagement with said second rack member to, when rotated, cause said body of said second support to move along said second rack member.

7. The apparatus as defined in claim 6 wherein said second rack member is fixedly connected to a ring member which is rotatable about said central axis.

8. The apparatus as defined in claim 7 further including a third manually rotatable knob carried by said ring member, said third manually rotatable knob being connected with a set screw engageable with said circular perimeter of said first support to lock said ring member in a position relative to said first support.

9. The apparatus as defined in claim 7 wherein said first support has a circular recess concentric with said central axis and said ring member is located in said recess.

10. The apparatus as defined in claim 7 wherein said ring member has a groove around its perimeter and said first support has a plurality of detents received in said groove for supporting said ring member for rotation relative to said first support and permitting removal of said ring member from said recess.

11. The apparatus as defined in claim 10 wherein each of said detents comprise a detent member for engaging said ring member, a spring biasing said detent member into engagement with said ring member, and a part threaded into said first support for adjusting the force applied by said spring to said detent member.

12. The apparatus as defined in claim 4 wherein said cannula gripper mechanism is a portion of a support arm for attachment to a mechanical arm and a manually movable member connected to said support arm for actuating a valve to vent vacuum applied to the mechanical arm through said support arm.

13. The apparatus as defined in claim 12 wherein said support arm includes first and second portions which are pivotal relative to each other about a pivot axis and a locking device for locking said first and second portions in a selected relative position.

14. An apparatus for use in percutaneous surgery, said apparatus comprising:
a cannula having a channel extending through the cannula, said channel having a central axis;
a first support connected with said cannula; and
a mechanism connecting said first support and said cannula for relative movement along said central axis, said mechanism comprising a gripper for gripping said cannula, a connection member connected to said gripper, and an adjustable member for moving said connection member and said gripper mechanism relative to said first support along said central axis.

15. The apparatus as defined in claim 14 wherein said connection member includes a rack member and said adjustable member includes a gear member.

16. The apparatus as defined in claim 14 wherein said gripper includes gripper arms which engage an outer surface of said cannula.

17. The apparatus as defined in claim 16 wherein said gripper arms are biased apart by a spring interposed between said gripper arms.

18. The apparatus as defined in claim 17 further including a pin extending through said gripper arms and a gripper actuating lever, said pin having an end projecting away from one of said arms; and said gripper actuating lever pivotally connected to said end and having a portion for moving said gripper arms together to grip said cannula when said gripper actuating lever is pivoted in a first direction and permitting said spring to move said gripper arms apart when said actuating lever is pivoted in a second direction opposite said first direction.

19. The apparatus as defined in claim 18 wherein said cannula gripper arms are portions of a support arm for attachment to a vacuum controlled arm to which vacuum is applied to prevent relative movement of parts of the vacuum controlled arm; and a manually movable member is connected to said support arm for actuating a valve to vent the vacuum applied to the vacuum controlled arm through said support arm.

20. An apparatus for use in percutaneous surgery, said apparatus comprising:
a cannula having a channel extending through said cannula, said channel having a central axis;
a first support associated with said cannula;
a second support for supporting a viewing element, the viewing element extending into said channel;
a structure connecting said first and second supports, said structure including a movable member for repositioning said first and second supports relative to each other along said central axis.

21. The apparatus as defined in claim 20 wherein said movable member includes a manually rotatable knob.

22. The apparatus as defined in claim 21 further comprising a rack connected with said first support, a gear carried by said second support and rotatable relative to said rack upon rotation of said manually rotatable knob to cause said first and second supports to move relative to each other along said central axis.

23. The apparatus as defined in claim 21 further including a cannula gripper mechanism attached to said first support.

24. The apparatus as defined in claim 23 further including a mechanism supporting said second support for rotation relative to said first support about said central axis.

25. The apparatus as defined in claim 24 wherein said cannula gripper mechanism comprises a part of a support arm for attachment to a vacuum controlled mechanical arm to which vacuum is applied to prevent relative movement of parts of the mechanical arm.

26. The apparatus as defined in claim 25 further including a valve adapted to vent the vacuum applied to the mechanical arm, said valve including a manually movable member connected to said support arm for actuating said valve to vent the vacuum applied to the mechanical arm through said support arm.

27. An apparatus for use in percutaneous surgery, said apparatus comprising:
a cannula having a channel extending through said cannula;

a mechanism for supporting said cannula, said mechanism including a support arm for attachment to a vacuum controlled mechanical arm to which vacuum is applied to prevent movement of parts of the mechanical arm;

a valve actuatable to vent the vacuum applied to the mechanical arm and including a manually movable member connected to said support arm for actuating said valve to vent the vacuum applied to the mechanical arm through said support arm.

28. The apparatus as defined in claim 27 wherein said support arm includes first and second portions which are pivotal relative to each other about a pivot axis and a locking device for locking said first and second portions in a selected relative position.

29. The apparatus as defined in claim 28 wherein said locking device includes meshing teeth on said first and second portions, said first and second portions extending around at least a part of said pivot axis and projecting axially relative to said pivot axis to intermesh, said locking device further including a fastener for holding said meshing teeth in engagement.

30. The apparatus as defined in claim 29 wherein one of said first and second portions has a threaded passage and said fastener extends through the other of said first and second portions and is screwed into said threaded passage.

31. The apparatus as defined in claim 28 wherein said support arm has a projecting portion defining a chamber and a connection for communicating said chamber with the vacuum in the mechanical arm; and said valve comprises a movable valve member for venting said chamber.

32. The apparatus as defined in claim 31 wherein said movable valve member is located in said chamber and said manually movable member is connected to said movable valve member and projects externally from said chamber.

33. An apparatus for use in percutaneous surgery, said apparatus comprising:

a cannula having a channel extending through said cannula, said cannula having a central axis;

a support for supporting a viewing element which extends into said channel; and a mechanism for adjusting the position of the viewing element in a direction transverse to said central axis.

34. The apparatus as defined in claim 33 wherein said mechanism includes an adjustable member for rotating the viewing element about an axis offset from and perpendicular to said central axis.

35. The apparatus as defined in claim 34 further including a threaded bore in said support for receiving said adjustable member, rotation of said adjustable member causing a change in the position of said viewing element.

36. The apparatus as defined in claim 34 wherein rotation of said adjustable member affects movement of said adjustable member along said central axis to cause rotation of said viewing element about said offset and perpendicular axis.

37. An apparatus for use in percutaneous surgery, said apparatus comprising:

a cannula having a channel extending through said cannula, said channel having a central axis;

a first member having an opening for said cannula, said opening having a center on said central axis; and a second member for supporting a viewing element which extends into said channel, said second member being rotatable relative to said first member, said second member further being rotatable about said central axis relative to said cannula.

38. An apparatus for use in percutaneous surgery, said apparatus comprising:

a cannula having a channel extending through said cannula, said channel having a central axis;

a first member having an opening for said cannula, said opening having a center on said central axis of said cannula; and a second member for operatively supporting a viewing element which extends into said channel, said second member and the viewing element being movable relative to said first member and said cannula.

39. The apparatus as defined in claim 38 further including a first mechanism for supporting said second member for rotation relative to said first member.

40. The apparatus as defined in claim 39 further including a second mechanism for axially adjusting said second member relative to said first member, said first mechanism being separate from said second mechanism.

41. An apparatus for use in percutaneous surgery, said apparatus comprising:

a first member having an opening for a cannula having a channel extending through the cannula, the channel having a central axis;

a second member for supporting a viewing element that extends into the cannula;

a first operable mechanism operable to axially move the viewing element relative to the cannula; and a second mechanism supporting both said second member and the viewing element for rotational adjustment of the viewing element about the axis of the cannula.

42. The apparatus as defined in claim 41 wherein said first mechanism is spaced apart from said second mechanism.

* * * * *